US006607890B1

(12) United States Patent
Nakatani et al.

(10) Patent No.: US 6,607,890 B1
(45) Date of Patent: Aug. 19, 2003

(54) MISMATCH-RECOGNIZING MOLECULES

(75) Inventors: Kazuhiko Nakatani, Kyoto (JP); Isao Saito, Kyoto (JP); Shinsuke Sando, Kyoto (JP)

(73) Assignee: Japan Science and Technology Corporation, Saitama (JP)

( * ) Notice: Subject to any disclaimer, the term of this patent is extended or adjusted under 35 U.S.C. 154(b) by 0 days.

(21) Appl. No.: 09/889,976

(22) PCT Filed: Oct. 26, 2000

(86) PCT No.: PCT/JP00/07497

§ 371 (c)(1),
(2), (4) Date: Jul. 24, 2001

(87) PCT Pub. No.: WO01/38571

PCT Pub. Date: May 31, 2001

(30) Foreign Application Priority Data

Nov. 26, 1999 (JP) .............................................. 11-336620

(51) Int. Cl.$^7$ .......................... C12Q 1/68; C07H 19/00; C07H 21/02; C07H 21/04
(52) U.S. Cl. .......................... 435/6; 536/23.1; 536/24.3
(58) Field of Search ............................. 435/6; 536/23.1, 536/24.3

(56) References Cited

FOREIGN PATENT DOCUMENTS

| JP | 2000-508876 | 2/2000 |
| JP | 2001-89478 | 4/2001 |
| WO | WO 00/50424 | 8/2000 |

OTHER PUBLICATIONS

"CORRIGENDA," Tetrahedron Letters, p. 2391, (1997).
"Abstracts of the 76th$^r$ National Meeting of the Chemical Society of Japan," p. 781 (Mar. 1999).

Nakatani et al., "Recognition of Guanine–Guanine Mismatches by the Dimeric Form of 2–Amino–1,8–napthyridine," Journal of the American Chemical Society, pp. 12650–12657 (2001).

Thomas, J., et al., *7–amido–1,8–naphthyridines as hydrogen bonding units for the complexation of guanite derivatives: the role of 2–alkoxyl groups in decreasing binding affinity*, Tetrahedron Letters, vol. 36, No. 42, pp. 7627–7630, (1995).

Nakatani et al., *Recognition of a Single Guanine Bulge by 2–Acylamino–1,8–naphtyridine*, J. Am. Chem. Soc., vol. 122, No. 10, pp. 2172–2177, (Mar. 2000).

Nakatani et al., *Scanning of guanine–guanine mismatches in DNA by synthetic ligands using surface plasmon resonance*, Nature Biotechnology, vol. 19, No. 1, pp. 51–55 (Jan. 2001).

*Primary Examiner*—Jezia Riley
(74) *Attorney, Agent, or Firm*—Rader, Fishman & Grauer PLLC

(57) ABSTRACT

A method whereby a mismatched base pair in a nucleic acid such as DNA or RNA can be conveniently and highly sensitively detected; and detection reagents therefor. A method comprising, in a base pair failing to form a normal base pair, forming a mimetic base pair with the use of a mismatch-recognizing molecule represented by the following general formula (I): A—L—B (I) wherein A represents a chemical structure moiety capable of forming a pair with one of the bases of the base pair failing to form a normal base pair; B represents a chemical structure moiety capable of forming a pair with the other of the bases of the base pair failing to form a normal base pair; and L represents a linker structure whereby the chemical structure moieties A and B are linked to each other; and measuring the formation of the above-described mimetic base pair to thereby detect and identify the base pair failing to form a normal base pair; kits therefor; reagents for detecting a mismatch; and a method of detecting an abnormality in the base sequence of a gene.

14 Claims, 3 Drawing Sheets

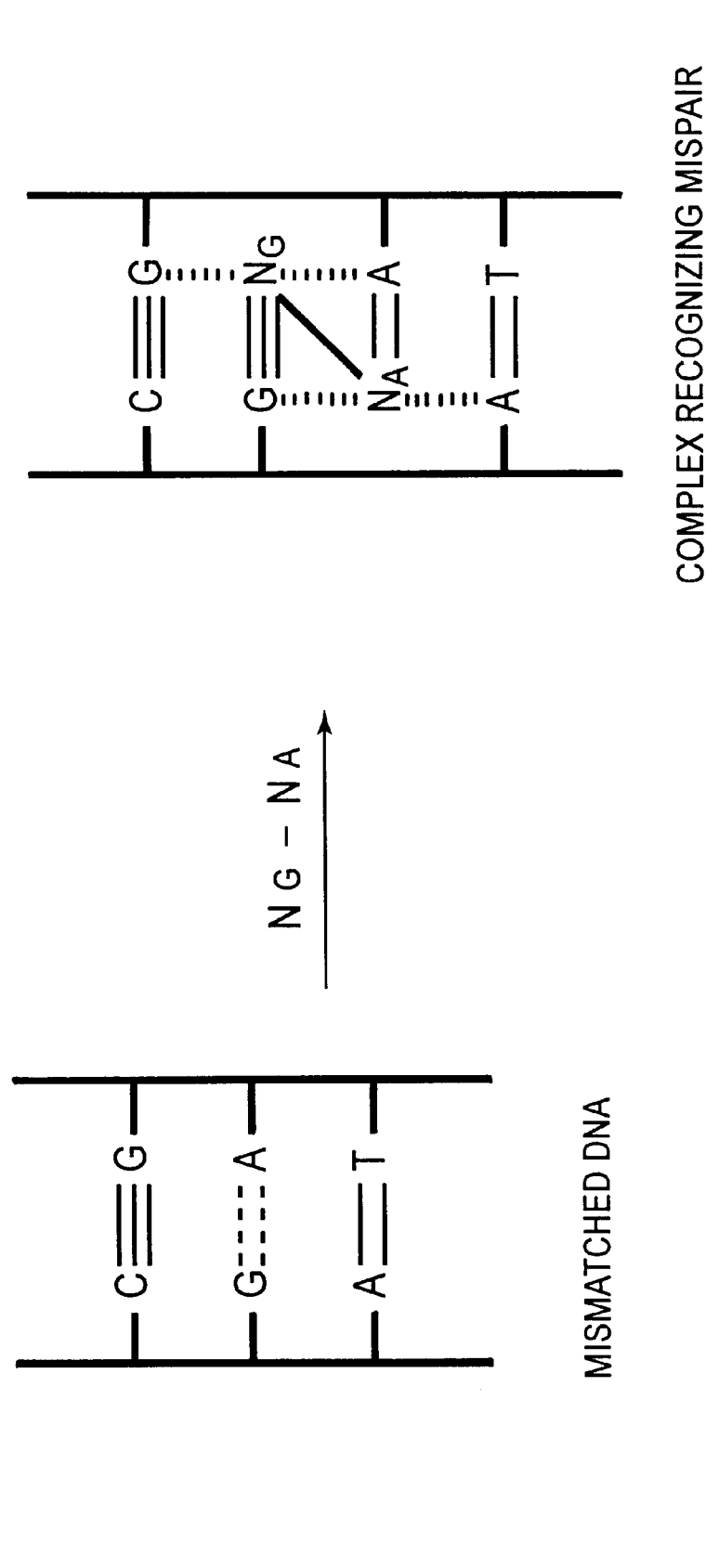

MISMATCH-RECOGNIZING MOLECULES

TECHNICAL FIELD

The present invention relates to a method for detecting or identifying a base pair, which can not construct a normal complementary base pairing, in base pairs, which can not construct a normal complementary base pairing, comprising making said base pair which can not construct a normal base pairing construct a pseudo-base-pairing, and assaying a formation of said pseudo-base-pairing, a reagent therefor, a kit containing the same, a compound therefore, and a method for detecting an abnormal base sequence in DNA or RNA using said method.

BACKGROUND ART

In a construction of a double-stranded structure by a hybridization of nucleic acids such as DNA and RNA, a base pair for constructing a base pairing is fixed. For example, these combinations are guanine (G) and cytosine (C), and adenine (A) and thymine (T). Generally, all bases hybridize by constructing such base parings, but sometimes, there is a case not constructing such a base pairing in some part of a base sequence.

For example, when some DNA and another DNA are placed under a condition to hybridize, almost all bases can construct such base pairings, but there is a case that one or several bases, may not able to construct such a base pairing. In the present specification, such a base pair, which can not construct a normal base pairing, is designated as mismatched base pair.

Recently, studies on various hereditary diseases caused by differences in one or more bases are in progress. For example, a hereditary disease having a gene, in which one base is different from the normal one [SNP (Single Nucleotide Polymorphism)] is known, and an elucidation for the hereditary disease is attracting an attention. If such gene hybridize with a normal gene, most of bases can hybridize and construct normal base pairings, but a mismatched base pairing may occur in one base pair.

At present, as a method for detecting such a mismatched base pair, a mean for comparing a hybridization efficiency of a double-stranded DNA is generally known. However, since the method needs a great effort because base sequences of the DNA containing the mismatched base pair should be known in advance in order to use the method, this is not a suitable method for treating a large number of specimens. Further, another method utilizing a selective binding of a DNA repair protein such as MutS to an injured position of a gene is known, but it is difficult to maintain an activity of the protein.

As explained above, detection of the part of a mismatched base pair in a hybridized DNA is very difficult and sensitivity is very low, consequently an establishment of a simple and highly sensitive detection method has been requested.

The present inventors developed a bulge DNA recognition molecule, which was a molecule specifically binding to a DNA (bulge DNA) having an unpaired base (bulge base) generated in a double-stranded DNA and stabilizing the same (JP-A-11-262205). The bulge DNA recognition molecule not only forms a hydrogen bond with an unpaired base but also is stabilized by intercalating in a space formed by a presence of the bulge base by utilizing stacking interactions between an aromatic ring and bases near by the bulge.

The present inventors further studied an action to the unpaired base utilizing a stacking effect in the presence of surrounding bases, and found that even in a position at the mismatched base pair, a compound having two molecular species which could construct base pairings was incorporated into the space relatively stably by the stacking effect.

DISCLOSURE OF THE INVENTION

The present invention provides a simple and high sensitive method for detecting such a mismatched base pair.

More particularly, the present invention provides a simple and high sensitive method for detecting a mismatched base pair in a double-stranded DNA and a reagent therefor.

The present invention relates to a method for detecting or identifying a base pair, which can not construct a normal complementary base pairing, in base pairs, which can not construct a normal complementary base pairing, comprising using a compound represented by the general formula (I):

$$A-L-B \qquad (I)$$

(wherein A is a chemical structural moiety constructing a complementary base pairing with a base in the base pair which can not construct a normal base pairing, B is a chemical structural moiety constructing another complementary base pairing with the other base in the base pair which can not construct a normal base pairing, and L is a linker structure linking the chemical structural moieties A and B), having a chemical structural moiety A and a chemical structural moiety B, both of which can construct base pairings with corresponding bases of the base pair, respectively, and a linker structure L linking said chemical structural moieties A and B, constructing a pseudo-base-pairing to said base pair which can not construct a normal base pairing, and assaying the construction of said pseudo-base-pairing.

Further, the present invention relates to a reagent for constructing a pseudo-base-pairing with a base pair which can not construct a normal base pairing comprising a compound represented by the general formula (I):

$$A-L-B \qquad (I)$$

(wherein A is a chemical structural moiety constructing a complementary base pairing with a base of a base pair which can not construct a normal base pairing, B is a chemical structural moiety constructing another complementary base pairing with the other base of the base pair which can not construct a normal base pairing, and L is a linker structure linking with the chemical structural moieties A and B), for constructing pseudo-base-pairings with a base pair which can not construct a normal base pair, in the method described above for detecting or identifying a base pair, which can not construct a normal base pairing, by constructing pseudo-base-pairings with a base pair which can not construct a normal base pairing and assaying the construction of said pseudo-base-pair.

Still further, the present invention relates to a kit comprising consisting of the above described reagent of the present invention and materials for detecting or identifying a base pair, which can not construct a normal complimentary base pairing, by constructing pseudo-base-pairings in a base pair, which can not construct a normal base pairing, and assaying said pseudo-base-pairing.

Furthermore, the present invention relates to a compound represented by the general formula (II):

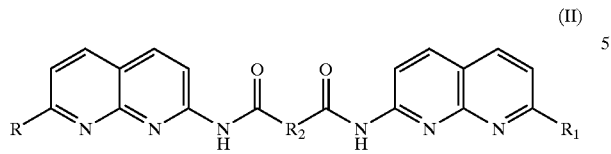

(II)

(wherein R and $R_1$ are a hydrogen atom, an alkyl group having 1 to 15 carbon atoms wherein one or more carbon atoms in said alkyl group are optionally substituted by oxygen atom or nitrogen atom, an alkoxy group having 1 to 15 carbon atoms wherein one or more carbon atoms in said alkoxy group are optionally substituted by oxygen atom or nitrogen atom, or a mono- or dialkylamino group having 1 to 15 carbon atoms wherein one or more carbon atoms in said alkylamino group are optionally substituted by oxygen atom or nitrogen atom; $R_2$ is an alkyl group having 1 to 20 carbon atoms wherein one or more carbon atoms in said alkyl group are optionally substituted by oxygen atom, nitrogen atom or carbonyl group), or immobilized form of said compound modified to a chemical structure which enables to immobilize the compound on a plate or a detecting apparatus for an instrumental analysis.

Still furthermore, the present invention relates to a method for detecting an abnormal base sequence in DNA or RNA comprising hybridizing a single-stranded DNA or RNA of a specimen and a corresponding DNA or RNA thereto having a normal base sequence, subsequently constructing pseudo-base-pairings with a base pair, which can not construct a normal base pairing, in said hybridized DNA or RNA by using a compound represented by the general formula (I):

A—L—B     (I)

(wherein A is a chemical structural moiety constructing a complementary base pairing with a base of a base pair which can not construct a normal base pairing, B is a chemical structural moiety constructing another complementary base pairing with the other base of the base pair which can not construct a normal base pairing, and L is a linker structure linking the chemical structural moieties A and B), having a chemical structural moiety A and a chemical structural moiety B, both of which can construct base pairings with corresponding bases of the base pair, respectively, and a linker structure L linking said chemical structural moieties A and B, assaying said pseudo-base-pairing, and detecting and identifying a base pair which can not construct a normal base pairing.

In the following explanation, the above description "a chemical structural moiety constructing a complementary base pairing with a base in a base pair which can not construct a normal base pairing [the parts of A and B in the general formula (I)] is sometimes simply designated as "base recognition site".

BRIEF DESCRIPTION OF THE DRAWINGS

FIG. 3 is a schematic drawing showing an action of the mismatched base recognition molecule of the present invention in the mismatched base site.

BEST MODE FOR CARRYING OUT THE INVENTION

Figure 1:
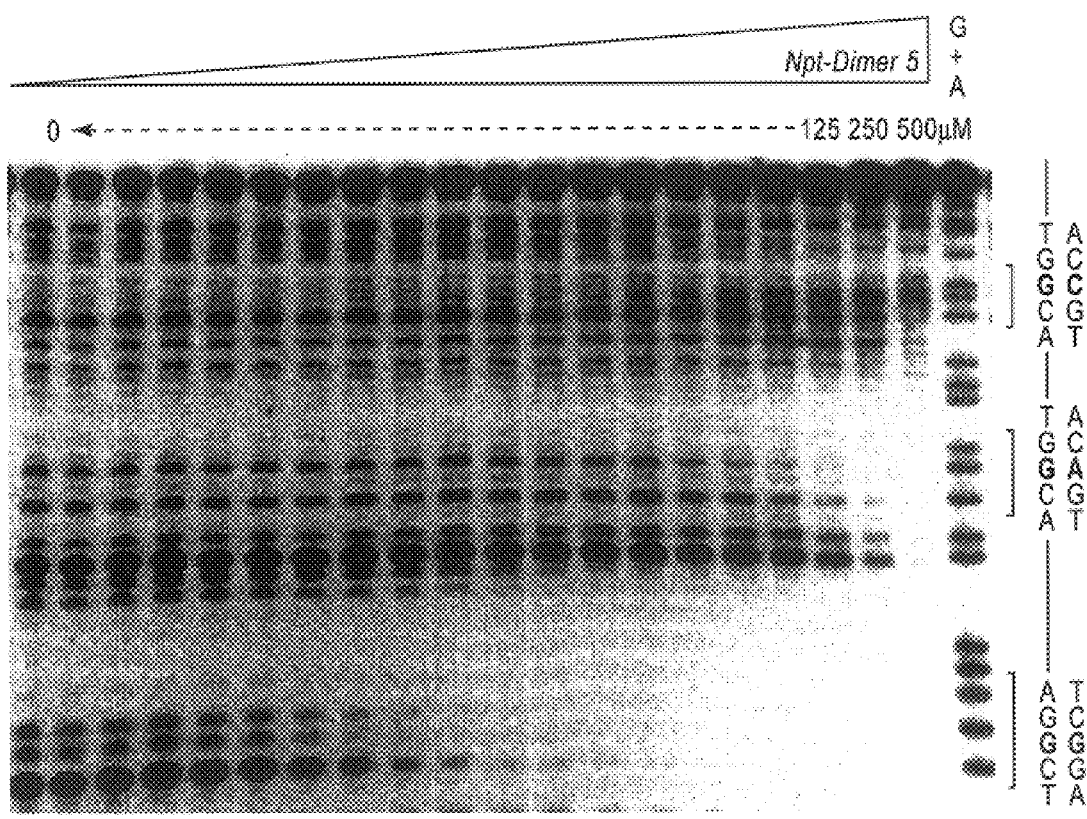
FIG. 1 is a photograph instead of drawing showing an inhibitory effect of the mismatched base recognition molecule of the present invention on a cleavage action of DNase I in the mismatched base site.

The present inventors developed a recognition molecule for a bulge DNA, which was a molecule specifically binding to a DNA (a bulge DNA) having an unpaired base (a bulge base) generated in a double-stranded DNA and stabilizing the same (JP-A-11-262205). The bulge DNA recognition molecule is intercalated in a space formed in an existence of the bulge base by utilizing a stacking interaction between an aromatic ring and the bases near by the bulge, and is stabilized. The present inventors found that as a result of binding the two bulge recognition molecules with linking chains such as a linker, each bulge recognition molecule constructs the same base pairing as the bulge base in the mismatched base region of the base pair. Moreover the present inventors found that these two bulge recognition molecules were incorporated into the DNA or RNA chains constructing a double-stranded chain in a comparatively stable form. The fact that such a relatively large molecular species is incorporated with a comparatively stable form is quite surprising thing. The present inventors found that a position of the mismatched base pairing in a hybridized nucleic acid can be simply specified by utilizing such a specific feature.

For example, 1,8-naphthyridine derivative, which can form hydrogen bond with guanine and can be stabilized by an action of a stacking effect of the surrounding bases, was linked with a linker to synthesize a dimer represented by the formula (III):

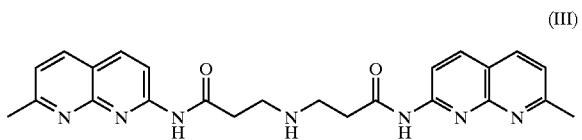

(III)

This compound constructs a pair with guanine at the 1,8-naphthyridine region. In a case when guanine is playing as a bulge base, since there is a sufficient space for constructing a pair of said guanine and 1,8-naphthyridine derivative, a formation of a pairing between 1,8-naphthyrlidine derivative and the bulge base can be confirmed simply by examining stabilities of both compounds. In a case of a mismatched base pairing, there is no sufficient space due to a presence of other base in the place for base pairing. Consequently, it is a big question whether such a large molecular species can be incorporated stably into such a small space between a base and a neighboring base.

Accordingly, it was examined whether such a compound having two 1,8-naphthylidien moieties can be incorporated into chains of a nucleic acid by constructing a paring with each mismatched guanine in a case when mismatched base pairing of guanine—guanine exists in a double-stranded nucleic acid. 52-mer double-stranded DNA labeled with 5'-$^{32}$P having a GC base pair, a GA mismatched base pair and a GG mismatched base pair in the double-stranded DNA was prepared. The partial sequences of the corresponding parts are illustrated as follows.

```
         *1          *2         *3
     .....ACCGT.....ACAGT.....TCGGA
     .....TGGCA.....TGGCA.....AGGCT
```

In the above double-stranded DNA, the part indicated by *1 is a normal G-C base pair; the part indicated by *2 is a mismatched base pair of G-A; and the part indicated by *3 is a mismatched base pair of G-G.

Using this double-stranded DNA, an inhibited position of DNA cleavage by DNase I was analyzed by means of DNase I (DNA hydrolase) footprinting titration in the presence of the compound of the formula (III) at various concentrations.

Results are shown in FIG. 1. FIG. 1 is a photograph instead of a drawing showing the results of an electrophoresis.

In FIG. 1, a concentration of the compound of the formula (III) is gradually increased from 0 up to 500 $\mu$M from left to right in the figure. Cleavage by DNase I (DNA hydrolase) is shown in black and inhibition in a position of the cleavage by DNase is shown in white.

For example, in a case of a normal base pairing of G-C, even if a concentration of the compound of the formula (III) is increased, no change of color, i.e. maintaining black, is observed, namely, cleavage by DNase I occurs. In a mismatched site such as the case of G-G, it is observed that the color gradually becomes more whiter, namely, the cleavage is gradually more inhibited as a concentration of naphthyrlidine of the formula (III) is increased. Such change is also observed at the mismatched site of G-A in a high concentration range.

Such inhibitory action against DNA hydrolase in a cleavage of DNA depends on an existence (including concentration) of the compound of the formula (III) and is thought to be a specific action of the compound of the formula (III).

Figure 2:
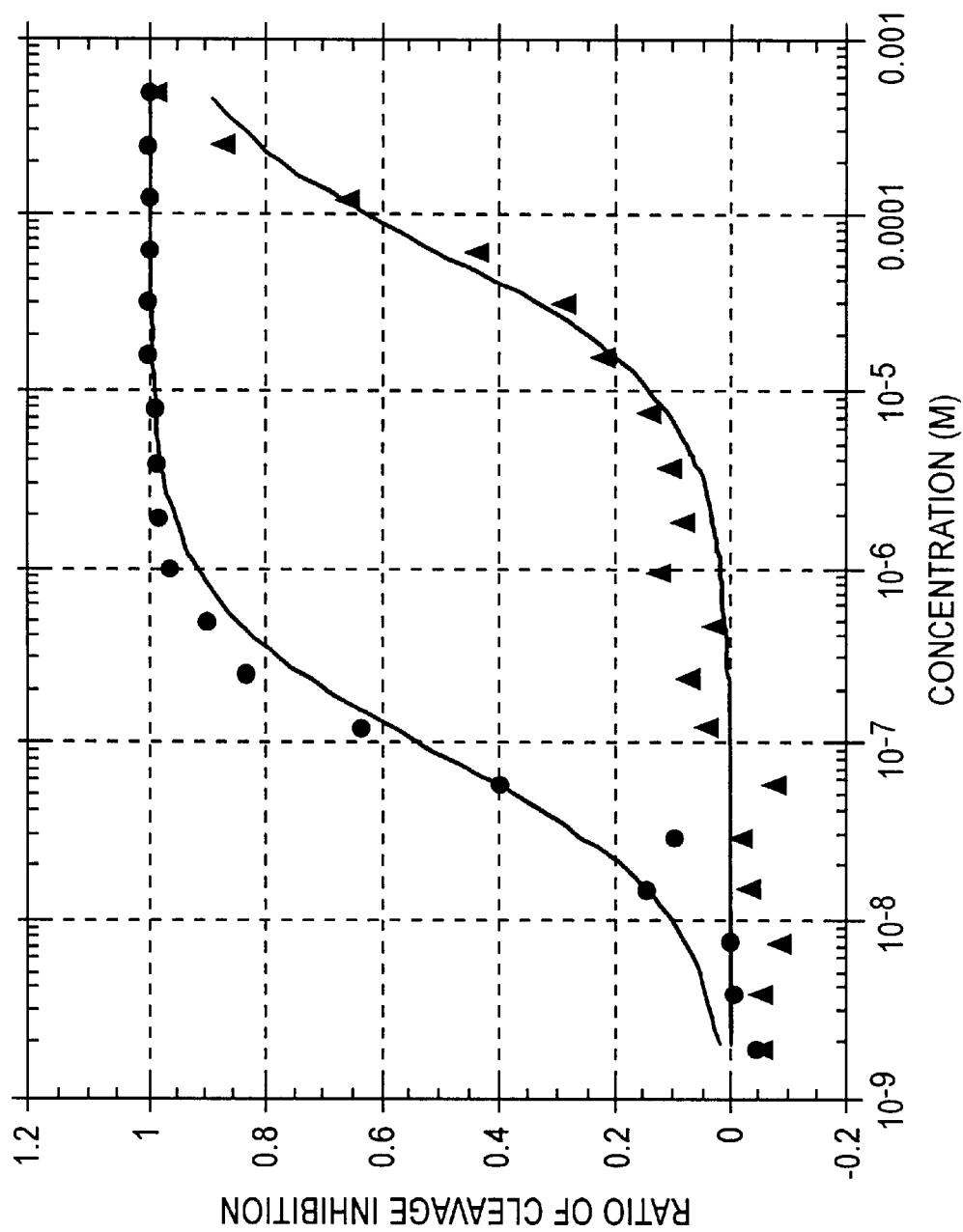
FIG. 2 is a graph showing an inhibitory effect for a cleavage action of DNase I using the mismatched base recognition molecule of the present invention.

FIG. 2 is a graph showing a relationship between an intensity of cleaved band and a concentration of added naphthyriidine in FIG. 1. In FIG. 2, the ordinate indicates an inhibitory ratio of cleavage obtained from an intensity of cleaved band, and the numeral "0.0" indicates an almost completely cleaved condition, and the numeral "1.0" indicates a condition in which the cleavage is almost completely inhibited. In FIG. 2, the abscissa indicates concentration (M) of the compound of the formula (III) added. In FIG. 2, black circle (●) in the graph indicates mismatched site of G-G, and black triangle (▲) indicates mismatched site of G-A.

As obvious from FIG. 2, the inhibitory action against cleavage in a mismatched site of G-G occurs from a comparatively low concentration and at the concentration about $10^{-5}$ M or more, the cleavage in the G-G mismatched site is inhibited almost completely. Also in the G-A mismatched site, the inhibitory action initiates from the concentration of approximately $10^{-6}$ M, and at around $5 \times 10^{-3}$ M (500 $\mu$M), an inhibition of about 90% of the cleavage is observed to occur.

As a result, a binding constant of the compound of the formula (III) to the mismatched base G-G [Ka (GGmis)] is calculated as $1.13 \times 10^7$ $M^{-1}$ and that to the mismatched base G-A [Ka (GAmis)] is calculated as $1.63 \times 10^4$ $M^{-1}$.

Ratio of both binding constants [(Ka (GGmis))/(Ka (GAmis))] is 696, consequently it can be understood that the compound of the formula (III) acts specifically to G-G mismatched base. From the fact that the binding constant of the compound of the formula (III) to the G-G mismatched base pair is comparatively large as the order of $10^7$ it is indicated that the compound of the formula (III) is incorporated stably into the G-G mismatched base pair site beyond expectation.

The mismatched base recognition molecule of the present invention incorporated into a double-stranded DNA constructs a comparatively stable base pair, and as a result of forming such base pair, new base sequence which can not be recognized by a natural enzyme may be constructed.

A schematic drawing showing comparatively stable intercalation of the compound represented by the formula (I) of the present invention (mismatched base recognition molecule) is illustrated in FIG. 3.

Left figure in FIG. 3 indicates a position of mismatched site of G-A in a double-stranded DNA. In the other region, normal base pairings are constructed, resulting a totally hybridized DNA although the mismatched site is found in the site of G-A. When the mismatched base recognition molecule of the present invention shown as $N_A$-$N_G$ is added therein, a condition as illustrated in the right figure in FIG. 3 is thought to occur. Namely, a mismatched base guanine (G) constructs a pair with a guanine recognition site ($N_G$) in the mismatched base recognition molecule, on the other hand, the other mismatched base adenine (A) constructs another pair with an adenine recognition site ($N_A$) in the mismatched base recognition molecule, and the guanine recognition site ($N_G$) and the adenine recognition site ($N_A$) in the mismatched base recognition molecule are linked with a linker (–) having a proper length and a proper flexibility, and the mismatched base recognition molecule is thought to be incorporated into a chain of a double-stranded DNA in a similar form as the other normal base pairs (refer to the right figure in FIG. 3).

The other major reason for the relatively stable incorporation of the mismatched base recognition molecule of the present invention into a chain of a double-stranded DNA is that a base recognition site of the mismatched base recognition molecule (for example, guanine recognition site ($N_G$) and adenine recognition site ($N_A$) described above) is stabilized by a stacking effect of the bases in front and behind (something like intermolecular force between bases). Dotted line in the right figure in FIG. 3 indicates the stacking effect of such bases. Since an interaction of $\pi$ electron system ($\pi$ stacking effect) is thought as one of factors generating such stacking effect, a degree of stacking effect may vary depending on types of the bases in front and behind, but binding of the molecule of the present invention and the mismatched base site may not be reduced significantly.

Consequently, the base recognition site of the mismatched base recognition molecule of the present invention [chemical structural moieties of A and B in the general formula (I)] should have a chemical structure not only to be able to form a hydrogen bond with an objective base but also to be able to obtain a stacking effect by the molecules in front and behind or surrounding.

As explained above, fundamental concept of the present invention is the finding that a compound in which two base recognition sites are bound with a linker having a proper length and a proper flexibility constructs a pairing specifically and stably in a mismatched site of base pairs in a double-stranded nucleic acid, and is not limited within the above explained G-G mismatched base pair.

In an embodiment described above, a mismatched base recognition molecule using 1,8-naphthyridine derivative which forms a stable hydrogen bond with guanine base as a base recognition site is shown with an example of a mismatched base pair of guanine (G)—guanine (G), but recognition of a mismatched base is not limited within the G-G mismatched base pair. The base recognition site in the mismatched base recognition molecule of the present invention can be selected from molecular species which can recognize a base of a mismatched base pair, construct a Watson-Crick type base pairing with the other base of the base pair and obtain a stacking effect by the surrounding bases, and includes molecular species which can construct a base pairing with various kinds of bases not limited in guanine.

For example, in a case when the mismatched base is cytosine, 2-aminonaphthyridine-4-one or derivatives thereof can be used as the base recognition site. Similarly, 2-quinolone derivatives, for example, 3-(2-aminoethyl-2-quinolone or derivatives thereof for a case when the mismatched base is adenine; and 2-aminonaphthyridine-7-one or derivative thereof for a case when the mismatched base is thymine can be used, respectively.

The base recognition site in the mismatched base recognition site of the present invention, which can be specifically recognized by the specific mismatched base, is preferably a structure having a heterocyclic aromatic group having a hydrogen bond site for forming hydrogen bond and a planar structure for constructing a stacking with neighboring bases, more preferably a structure having a heterocyclic aromatic group having a substituent with some degree of steric hindrance in order to enhance a selectivity for a base.

These substituents includes, for example, a linear or branched alkyl group having 1 to 15 carbon atoms, preferably 1 to 10 carbon atoms, and more preferably 1 to 7 carbon atoms; an alkoxy group comprising a linear or branched alkyl group having 1 to 15 carbon atoms, preferably 1 to 10 carbon atoms, and more preferably 1 to 7 carbon atoms; and a mono- or dialkylamino group having one or two substituents of linear or branched alkyl group having 1 to 15 carbon atoms, preferably 1 to 10 carbon atoms, and more preferably 1 to 7 carbon atoms.

One or more carbon atoms in these alkyl, alkoxy or mono- or dialkylamino groups may optionally be substituted by oxygen atom or nitrogen atom.

The linker structure L in the compound represented by the general formula (I) of the present invention is not specially limited if it can provide two base recognition sites with a proper length and a proper flexibility. It includes, for example, a linear or branched and saturated or unsaturated alkyl group having 1 to 15 carbon atoms, preferably 1 to 10 carbon atoms, and more preferably 1 to 7 carbon atoms, wherein one or more carbon atoms may optionally be substituted by oxygen atom, nitrogen atom or carbonyl group. A preferable linker includes a compound having amide linkage moieties in both ends and a nitrogen atom in the center, like a compound of the formula (III) described above.

The linker structure binds not only two base recognition sites but also a branch for immobilizing on a carrier at the linker structure. For example, if necessary, it can be immobilized on a carrier, by extending a branch such as alkylene group, which has a functional group for binding on a carrier in an end, from the position of a nitrogen atom at around the center of the linker.

The bonding between the base recognition site A or B and the linker structure L in the general formula (I) of the present invention may be by a carbon-carbon bond, but preferably by a functional group because of an easiness of synthesis. Functional groups for the bonding includes various types such as ether linkage, ester linkage, amide linkage, linkage with phosphate, and the like, and among them an amide linkage is preferable.

Example of the compound of the general formula (I) preferable for G-G mismatched base in the mismatched base recognition molecule of the present invention is the compound represented by the general formula (II):

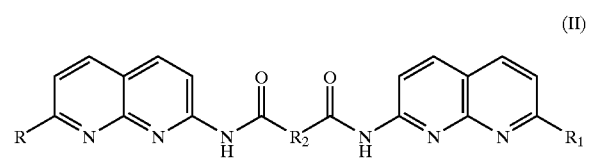

(II)

(wherein R and $R_1$ are a hydrogen atom, an alkyl group having 1 to 15 carbon atoms wherein one or more carbon atoms in said alkyl group are optionally substituted by oxygen atom or nitrogen atom, an alkoxy group having 1 to 15 carbon atoms wherein one or more carbon atoms in said alkoxy group are optionally substituted by oxygen atom or nitrogen atom, or a mono- or dialkylamino group having 1 to 15 carbon atoms wherein one or more carbon atoms in said alkylamino group are optionally substituted by oxygen atom or nitrogen atom, $R_2$ is an alkyl group having 1 to 20 carbon atoms wherein one or more carbon atoms in said alkyl group are optionally substituted by oxygen atom, nitrogen atom or carbonyl group), or immobilized form of said compound. "Immobilized form" herein means that the compound described above is in a state immobilized on a carrier or having an extended "branch" for immobilization described above.

The alkyl group of $R_2$ is a divalent alkyl group as shown in the general formula (II).

The mismatched base recognition molecule of the present invention can be used alone, or it can be used in a labeled form, for example, by introducing a radioactive element or a chemiluminescent or fluorescent molecular species into the extended branch for immobilization from the linker structure or the linker itself. Labeling as a assaying mean can be made by labeling at a nucleic acid moiety of DNA or RNA as a detection object.

Furthermore, the mismatched base recognition molecule of the present invention can be used by immobilizing by binding to a polymer material such as polystyrene directly or via an alkylene group at a suitable position of the molecule.

The mismatched base recognition molecule of the present invention is an organic compound of low molecular weight and is produced by a conventional organic synthesis. For example, the above described 1,8-naphthyridine derivative can be produced by reacting 1-amino-1,8-naphthyridine or 2-amino-7-methyl-1,8-naphthyridine with reactive derivatives of N-protected-4-aminobutyric acid such as acid chloride, acylating the amino group at position-2, and removing the protective group of the amino group. As a protective group, the protective groups for amino group used in the peptide synthesis, for example, hydrochloride, acyl group and alkoxycarbonyl group can be used.

The objective mismatched base recognition molecule can be obtained by reacting thus obtained base recognition site with a compound for linker having carboxyl groups or reactive derivatives thereof in both ends. If a reactive group such as nitrogen atom exists in a molecule of the compound for linker, the compound can be used by suitably protecting with the above described protective group.

The mismatched base recognition molecule of the present invention can be used as a reagent or detection agent for detecting a mismatched base pair, or it can be prepared as a composition for detecting a mismatched base pair by combining with a proper carrier. It can also be used as a base pair formation agent for constructing a pseudo-base-pairing for a base pair which can not construct a normal base pairing. "Pseudo-base-pair" herein means a base pair different from a naturally occurring base pairs, and does not mean strength of a base pairing. "Normal base pair" used in the present invention means naturally occurring base pairs, such as G-C, A-T or A-U.

Further, the present invention provides a kit for detecting or identifying a base pair, which can not construct a normal base pair, by constructing a pseudo-base-pairing in a base pair, which can not construct a normal base pairing, comprising consisting of a mismatched base recognition molecule of the present invention and materials for detecting or identifying the base pair, for example, materials such as a reagent for chemiluminescence and fluorescence and buffer, and assaying said pseudo-base-pairing.

Furthermore, the present invention provides a method for detecting, identifying or quantifying a mismatched base pair in DNA by using a mismatched base recognition molecule of the present invention or a labeled or immobilized mismatched base recognition molecule of the present invention.

By using the base recognition site of the mismatched base recognition molecule of the present invention, in a DNA having one or more mismatched base paring, it is possible not only to stabilize the DNA by forming a hydrogen bond with a specific base pair such as G-G mismatch and G-A mismatch, but also to obtain a comparatively stable DNA by allowing to be stacked by the surrounding, preferably the neighboring base pairs, in spite of an existence of the mismatched base pairing.

Consequently, the present invention provides a DNA containing a mismatched base pair, in which the mismatched base pair is stabilized by forming a hydrogen bond between the base recognition site of the mismatched base pair recognition molecule of the present invention and each base in the specific mismatched base pair and being stacked by base pairs present near said base.

The DNA of the present invention is characterized by constructing a "pair" (pseudo-base-pair) similar to a base pair by forming a hydrogen bond between the mismatched base pair and the base recognition site of the mismatched base recognition molecule of the present invention, and the base recognition site of the mismatched base recognition molecule of the present invention constructing a "pair" with the mismatched base being stacked by the surrounding, preferably the neighboring bases constructing base pairs in a sandwich structure.

By using the mismatched base pair recognition molecule of the present invention, detection, identification or quantification of a mismatched base pair, which can not be achieved by a prior art, can be performed with high sensitivity and simplicity, and a DNA which is specific to the mismatched base pair and stable can be constructed. Therefore, the mismatched base recognition molecule of the present invention can be applied for treatment, prevention or diagnosis of various diseases involving DNA damage.

Further, since the DNA of the present invention can be maintained relatively stably in a form bearing the mismatched base pair, it can be applied for stabilization of a DNA containing a mismatched base pair as well as materials for study to elucidate a cause for generation of the mismatch or mechanism of mismatch repair.

The present invention further provides a method for detecting an abnormal base sequence in DNA or RNA comprising hybridizing a single-stranded DNA or RNA of a specimen and the corresponding DNA or RNA thereto having a normal base sequence, subsequently constructing a pseudo-base-pairing with a base pair, which can not construct a normal base pairing, in said hybridized DNA or RNA by using the mismatched base pair recognition molecule of the present invention described above, assaying said pseudo-base-pairing, and detecting and identifying a base pair which can not construct a normal base pairing. The method can be applied for detecting an existence of an abnormality in a gene.

For example, the DNA suspected to have an abnormality or its transcription product RNA is collected, and hybridized with a complementary DNA or RNA having a normal base sequence to form a double-stranded nucleic acid. If a base sequence in the collected gene has an abnormality, a mismatched base pair is formed at the abnormal site of the base. The pseudo-base-pairing described above is constructed by adding the mismatched base pair recognition molecule of the present invention to the double-stranded nucleic acid bearing a mismatched base pair. The abnormality of the collected gene can be detected and identified simply and with a high sensitivity by assaying the molecule having the newly constructed base pair.

As a mean for assaying the newly constructed base pair (base pairing with the mismatched base pair recognition molecule of the present invention and the mismatched base pair) described above, chemiluminescence, fluorescence or radioisotope labeling can be used. Since the mismatched base pair recognition molecule of the present invention is a organic compound of low molecular weight and said molecule is incorporated into the nucleic acid in a case of forming the new base pairing, the unreacted mismatched base pair recognition molecule of the present invention and nucleic acids can be separated relatively easily.

As described above, the mismatched base pair recognition molecule can be used in an immobilized state on a carrier. For example, the mismatched base pair recognition molecules of the present invention specific to various mismatched base pairings are immobilized on plates such as titer plate; the double-stranded nucleic acid described above, preferably labeled nucleic acid is added thereto; and after an incubation for several minutes, the nucleic acids are removed; as a result, the nucleic acid, which is specifically reacted with the mismatched base pair recognition molecule of the present invention, is trapped by the mismatched base pair recognition molecule of the present invention, and can be detected and identified by the labeling.

Moreover, the mismatched base pair recognition molecule of the present invention can be immobilized on a metal thin film of a detection chip of the surface plasmon resonance (SPR). In the case using this SPR, an existence of the mismatched base pairing can be specifically detected only by flowing a specimen containing the double-stranded nucleic acid described above on the surface of the detection chip.

The mismatched base pair recognition molecule of the present invention can also be applied for other various detection means, and the present invention is not limited within these specific detection means.

EXAMPLES

The present invention will be explained in detail by various concrete experimental examples, but is not limited within these concrete examples.

Example 1

Synthesis of the Compound of the Formula (III)

The compound in the title was synthesized according to the following chemical reactions.

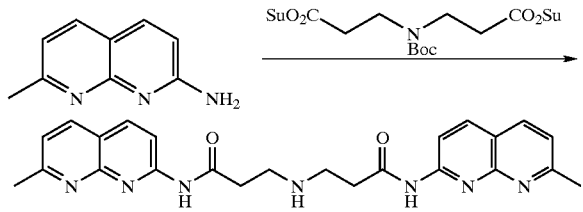

(wherein Boc is t-butoxycarbonyl.)

Succinimidyl ester of N-Boc-dicarboxylic acid (313 mg, 0.74 mmol) was dissolved in chloroform (15 ml), and 2-amino-7-methyl-1,8-naphthyridine (294 mg, 1.85 mmol) was added thereto. After reacting at room temperature for 48 hours, Boc-dinaphthylidinamide was obtained by the post-treatment of the reaction mixture. Boc-dinaphthylidinamide is dissolved in ethyl acetate containing 4N-HCl and reacted at room temperature for 2 hours to obtain dinaphthylidinamide in the title with overall yield 13%.

$^1$H NMR (CD$_3$OD,400 MHz) δ:8.26(d,2H,J=8.8 Hz), 8.14(d,2H,J=8.8 Hz), 8.11(d,2H,J=8.0 Hz), 7.34(d,2H,J=8.0 Hz), 3.20(t,4H,J=6.0 Hz), 2.84(t,4H,J=6.0 Hz), 2.68(s,6H); FABMS (NBA), m/e (%): 444 [(M+H)$^+$, 10], 246 (40), 154 (100) HRMS Calculated: C$_{24}$H$_{26}$O$_2$N$_7$ [(M+H)+] 444.2146. Found: 444.2148

Example 2

A double-stranded DNA was prepared by hybridizing 5'-end $^{32}$P labeled 52-mer DNA to form mismatched base pairs with G-G and G-A (refer to the right figures in FIG. 1).

Various concentrations of the compound obtained in example 1 were added to the double-stranded DNA, and analyzed by DNA footprinting using DNase I.

The double-stranded DNA (<4 nM strand concentration) was incubated with the compound obtained in example 1, which was adjusted to various concentrations with tris-HCl buffer (10 mM, pH 7.6) containing NaCl (100 mM) and MgCl$_2$ (5 mM), at 4° C. for 12 hours. 0.2 U DNase I (DNA hydrolase) was added thereto and incubated at 25° C. for 8 hours. DNA was recovered by mans of ethanol precipitation and electrophoresed using a gel containing 12% polyacrylamide and 7M urea.

Results are shown in FIG. 1.

INDUSTRIAL APPLICABILITY

Using the mismatched base pair recognition molecule of the present invention, a mismatched base pair such as guanine—guanine mismatch can easily be detected with a high sensitivity. Such a detection could not be achieved by the prior art.

What is claimed is:

1. A method for detecting or identifying a base pair which can not construct a normal complementary base pairing, comprising:

constructing a pseudo-base-pairing between said base pair and a compound represented by the general formula (I):

A—L—B    (I)

wherein A is a chemical structural moiety constructing a complementary base pairing with a base of a base pair which can not construct a normal base pairing, B is a chemical structural moiety constructing a complementary base pairing with the other base of the base pair which can not construct a normal base pairing, and L is a linker structure linking the chemical structural moieties A and B, and assaying the formation of said pseudo-base-pairing.

2. The method according to claim 1, wherein the chemical structural moieties A and B of the compound represented by the general formula (I) constructs base pairings with bases by forming hydrogen bond with bases, and being stabilized by a stacking effect of the surrounding bases.

3. The method according to claim 1, wherein the chemical moieties A and B in the compound represented by the general formula (I) have a heterocyclic aromatic group containing 2 or more chemical structural moieties which can form hydrogen bond with bases.

4. The method according to claim 3, wherein at least one of the chemical structural moieties of A and B in the compound represented by the general formula (I) is napthyridine or its derivatives represented by the following formula:

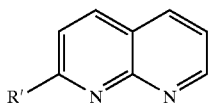

wherein R' is selected from the group consisting of an alkyl group having 1 to 15 carbon atoms with at least one carbon atom in said alkyl group being optionally substituted by an oxygen atom or a nitrogen atom, an alkoxy group having 1 to 15 carbon atoms with at least one carbon atom in said alkoxy group being optionally substituted by an oxygen atom or a nitrogen atom, and a mono- or di-alkylamino group having 1 to 15 carbon atoms with at least one carbon atom in said alkylamino group being optionally substituted by an oxygen atom or a nitrogen atom.

5. The method according to claim 1, wherein the linkage of the chemical structural moieties A and B to the linker structure L in the compound represented by the general formula (I) is a carboxylic amide linkage.

6. The method according to claim 1, wherein the compound represented by the general formula (I) is the compound represented by the general formula (II):

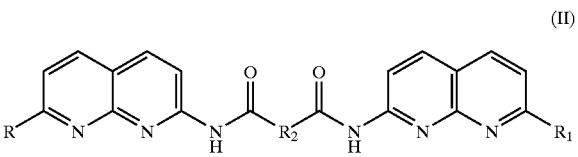

(wherein R and R$_1$, are a hydrogen atom, an alkyl group having 1 to 15 carbon atoms wherein one or more carbon atoms in said alkyl group are optionally substituted by oxygen atom or nitrogen atom, an alkoxy group having 1 to 15 carbon atoms wherein one or more carbon atoms in said alkoxy group are optionally substituted by oxygen atom or nitrogen atom, or a mono- or dialkylamino group having 1 to 15 carbon atoms wherein one or more carbon atoms in said alkylamino group are optionally substituted by oxygen atom or nitrogen atom; R$_2$ is an alkyl group having 1 to 20 carbon atoms wherein one or more carbon atoms in said alkyl group are optionally substituted by oxygen atom, nitrogen atom or carbonyl group).

7. The method according to claim 1, wherein the compound represented by the general formula (I) is immobilized on a carrier.

8. The method according to claim 1, wherein the compound represented by the general formula (I) is labeled.

9. A reagent comprising a compound represented by the general formula (I):

wherein A is a chemical structural moiety capable to construct a complementary base pairing with a base of a base pair which can not construct a normal base pairing, B is a chemical structural moiety capable to construct another complementary base pairing with the other base of the base pair which can not construct the normal base pairing, and L is a linker structure linking chemical structural moieties A and B, which may be used in the method according to any of claims 1 to 8.

10. The reagent according to claim 9, wherein the reagent is a base pair forming agent to construct a pseudo-base-pairing in a base pair which can not construct a normal base pairing.

11. A kit comprising the reagent according to claim 9 and materials for detecting or identifying a base pair which can not construct a normal complementary base pairing, said materials being used in a method which comprises detecting or identifying said base pair which can not construct a normal complementary base pairing, constructing a pseudo-base-pairing in said base pair which can not construct a normal base pairing, and assaying the formation of said pseudo-base-pairing.

12. A compound represented by the general formula (II):

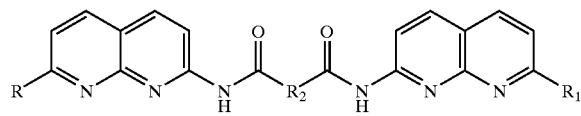

(wherein R and $R_1$ are a hydrogen atom, an alkyl group having 1 to 15 carbon atoms wherein one or more carbon atoms in said alkyl group are optionally substituted by oxygen atom or nitrogen atom, an alkoxy group having 1 to 15 carbon atoms wherein one or more carbon atoms in said alkoxy group are optionally substituted by oxygen atom or nitrogen atom, or a mono- or dialkylamino group having 1 to 15 carbon atoms wherein one or more carbon atoms in said alkylamino group are optionally substituted by oxygen atom or nitrogen atom, $R_2$ is an alkyl group having 1 to 20 carbon atoms wherein one or more carbon atoms in said alkyl group are optionally substituted by oxygen atom, nitrogen atom or carbonyl group), or an immobilized form thereof.

13. The compound according to claim 12, wherein the compound represented by the general formula (II) is the compound of the general formula (III):

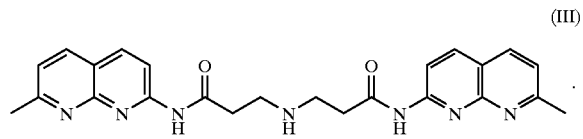

14. A method for detecting an abnormal base sequence in DNA or RNA comprising hybridizing a single-stranded DNA or RNA of a specimen and the corresponding DNA or RNA thereto having a normal base sequence, subsequently constructing a pseudo-base-pairing with a base pair, which can not construct a normal base pairing, in said hybridized DNA or RNA by using a compound represented by the general formula (I):

(wherein A is a chemical structural moiety constructing a complementary base pairing with a base of a base pair which can not construct a normal base pairing, B is a chemical structural moiety constructing another complementary base pairing with the other base of the base pair which can not construct a normal base pairing, and L is a linker structure linking the chemical structural moieties A and B), having a chemical structural moiety A and a chemical structural moiety B, both of which can construct base pairings with corresponding bases of the base pair, respectively, and a linker structure L linking said chemical structural moieties A and B, assaying the construction of said pseudo-base-pairing.

* * * * *